(12) United States Patent
Satishkumar et al.

(10) Patent No.: US 12,106,833 B2
(45) Date of Patent: Oct. 1, 2024

(54) CUSTOMIZING HEALTHCARE APP OFFERINGS BASED ON CLINICAL RECORDS

(71) Applicant: CERNER INNOVATION, INC., Kansas City, KS (US)

(72) Inventors: Manoj Satishkumar, Bangalore (IN); Nishchitha Subraya Gowda, Bangalore (IN); Subhadeep Das, Alipurduar (IN)

(73) Assignee: CERNER INNOVATION, INC., Kansas City, MO (US)

( * ) Notice: Subject to any disclaimer, the term of this patent is extended or adjusted under 35 U.S.C. 154(b) by 115 days.

(21) Appl. No.: 16/235,857

(22) Filed: Dec. 28, 2018

(65) Prior Publication Data

US 2019/0206530 A1 Jul. 4, 2019

Related U.S. Application Data

(60) Provisional application No. 62/612,114, filed on Dec. 29, 2017.

(51) Int. Cl.
| | |
|---|---|
| *G06F 16/954* | (2019.01) |
| *G06F 16/955* | (2019.01) |
| *G16H 10/60* | (2018.01) |
| *G16H 50/00* | (2018.01) |

(52) U.S. Cl.
CPC ........... *G16H 10/60* (2018.01); *G06F 16/954* (2019.01); *G06F 16/955* (2019.01); *G16H 50/00* (2018.01)

(58) Field of Classification Search
CPC ........ G16H 10/60; G16H 50/00; G16H 80/00; G06F 16/955; G06F 16/954
See application file for complete search history.

(56) References Cited

U.S. PATENT DOCUMENTS

| | | | | |
|---|---|---|---|---|
| 2001/0034631 A1* | 10/2001 | Kiselik | ................... | G06Q 30/02 705/2 |
| 2010/0023478 A1* | 1/2010 | Chandrasekar | ..... | G06F 16/8365 707/E17.017 |
| 2012/0316955 A1* | 12/2012 | Panguluri | ........... | G06F 16/9535 705/14.41 |
| 2013/0086160 A1* | 4/2013 | Rajaram | ................ | G06Q 50/01 709/204 |
| 2013/0339052 A1* | 12/2013 | Neff | ....................... | G06Q 30/02 705/3 |

(Continued)

*Primary Examiner* — Jonathan Ng
*Assistant Examiner* — Benjamin L. Hanks
(74) *Attorney, Agent, or Firm* — Kraguljac Law Group, LLC

(57) ABSTRACT

Methods, computer readable media, and systems for providing a Unified Medical Record (UMR) Cloud Network that takes maintenance and access of patient-centric healthcare records to the next level by providing a healthcare-provider-specific app store in a healthcare web portal by utilizing Fast Healthcare Interoperability Resources (FHIR) resources are provided. The UMR Cloud Network serves as a patient web portal which hosts a provider-specific FHIR App Store. The FHIR apps that reside in the provider-specific FHIR App Store may be designed to utilize patient-centric data and the subject patient's associated FHIR resources to provide individual solutions. In embodiments, the FHIR apps installed from the provider-specific FHIR App Store may be presented on a dashboard associated with the subject patient and provided by the UMR Cloud Network.

20 Claims, 16 Drawing Sheets

(56) References Cited

U.S. PATENT DOCUMENTS

| | | | |
|---|---|---|---|
| 2014/0114758 A1* | 4/2014 | Bentley | G06Q 30/0277 |
| | | | 705/14.53 |
| 2014/0172450 A1* | 6/2014 | Repko | G16H 10/60 |
| | | | 705/2 |
| 2014/0173443 A1* | 6/2014 | Hawkins, III | G06F 9/44505 |
| | | | 715/733 |
| 2014/0337353 A1* | 11/2014 | Hickey | G06F 19/00 |
| | | | 707/741 |
| 2016/0210427 A1* | 7/2016 | Mynhier | G16H 10/60 |
| 2017/0011182 A1* | 1/2017 | Whitehurst | G16H 40/63 |
| 2017/0329820 A1* | 11/2017 | Park | G06F 16/24522 |
| 2018/0233225 A1* | 8/2018 | Experton | G16H 20/60 |
| 2018/0369039 A1* | 12/2018 | Bhimavarapu | A61G 7/10 |
| 2020/0066384 A1* | 2/2020 | Tahmasebi Maraghoosh | |
| | | | G16H 15/00 |
| 2020/0066414 A1* | 2/2020 | Neff | G16H 10/20 |
| 2020/0242303 A1* | 7/2020 | Hwang | G06F 21/32 |

* cited by examiner

CUSTOMIZING HEALTHCARE APP OFFERINGS BASED ON CLINICAL RECORDS

CROSS-REFERENCE TO RELATED APPLICATIONS

This application claims priority to U.S. Provisional Patent Application No. 62/612,114, entitled "CUSTOMIZING HEALTHCARE APP OFFERINGS BASED ON CLINICAL RECORDS" and filed on Dec. 29, 2017, which application is hereby incorporated by reference as if set forth in its entirety herein.

FIELD

The present embodiments relate to a framework for hosting a healthcare-related app store. More specifically, the present embodiments relate to a framework for providing a patient-specific web-based healthcare portal and hosting an app store that is customized for a client of a healthcare app store host and surfaced through the patient portal. Present embodiments further relate to a framework that provides a patient-specific web-based healthcare portal that utilizes patient-specific data to surface a custom app offering via a patient dashboard.

BACKGROUND

Information Technology Systems (e.g., Electronic Health Records (EHRs), Computerized Physician Order Entry (CPOE) Systems, etc.) continue to play a significant role in cost reduction, as well as quality measurement and improvement for healthcare. Clinical records are now used, not only as a comprehensive record of healthcare, but also as a source of data for clinical decision support, hospital service activity reporting, hospital performance monitoring, and for audit and research. Thus, the importance of accurate content and convenient yet secure availability of clinical records is ever increasing.

As society becomes more transient with respect to residences, employers, healthcare insurance providers, healthcare service providers, and the like, it is increasingly difficult for patients and/or healthcare providers to maintain comprehensive clinical records, let alone to recall with any significant level of accuracy, details surrounding patients' clinical histories. As such, it is advantageous for patients and healthcare providers alike to be able to access patient-centric clinical records (including, by way of example only, family history, medication history, surgical history, and the like) from various physical locations over particular patients' lifetimes. Access to such patient-centric clinical records through online web-based healthcare portals have emerged in recent years that have served as a way to make this data more easily accessible to patients and providers than prior approaches (e.g., paper-based approaches). In some instances, online web-based healthcare portals have provided enhanced usability for patients and healthcare providers seeking access to patient-centric clinical records by providing a patient-centric dashboard from which a particular patient's records may be accessed. A dashboard may include, for instance, various tabs and/or icons, selection of which may link a user to particular patient-centric data relevant to a content title associated with a particular tab and/or icon.

BRIEF SUMMARY

The present disclosure relates to a framework for providing a Unified Medical Record (UMR) Cloud Network that takes maintenance and access of patient-centric healthcare records to the next level by providing an app store maintained by a healthcare app host in a healthcare web portal by utilizing Fast Healthcare Interoperability Resources (FHIR) resources. In aspects, the UMR Cloud Network serves as a patient web portal which hosts an app store containing apps specified by a healthcare app host. The apps that reside in the healthcare-app-host-specific app store may be designed to utilize patient-centric data (i.e., healthcare and/or other clinically-relevant data associated with a subject patient) and the subject patient's associated FHIR resources to provide individual solutions. In embodiments, the apps installed from the healthcare-app-host-specific app store may be presented on a dashboard associated with the subject patient and provided by the UMR Cloud Network. Thus, the UMR Cloud Network allows the utilization of FHIR resources of a patient and enables an app-store approach specifically for FHIR. This enables patients to have a web portal containing apps that provide individual, customized solutions. The web portal aims at eliminating the need for a patient to maintain medical documentation, clinical reports, medication history reports, medical consultation history, etc. over his/her lifespan. The FHIR RESTful APIs enable the UMR Cloud Network and the hosted FHIR apps to process and provide customized solutions. The UMR architecture also enables developers (provider and/or third-party) with UMR APIs to develop FHIR apps.

This Summary is provided to introduce a selection of concepts in a simplified form that are further described in the following Detailed Description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

The components and the figures are not necessarily to scale, emphasis instead being placed upon illustrating the principles of embodiments of the disclosure. Moreover, in the figures, like reference numerals designate corresponding parts throughout the different views.

DETAILED DESCRIPTION

Figure 1:
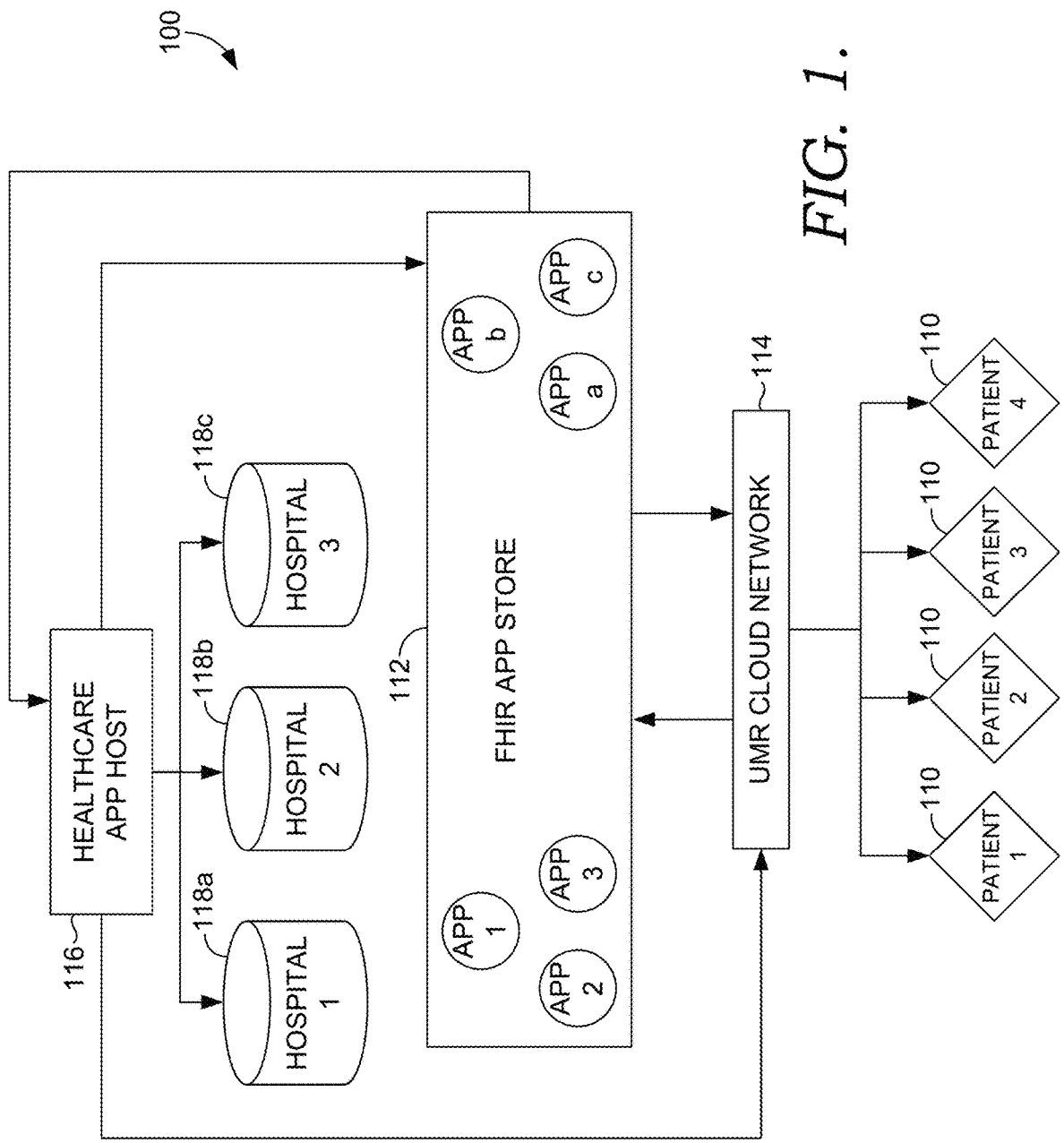
FIG. 1 is a schematic diagram illustrating a healthcare-app-host-specific FHIR App Store enabling UMR cloud network hosting of FHIR healthcare-related apps, in accordance with embodiments of the present disclosure.

The subject matter herein is described with specificity to meet statutory requirements. However, the description itself is not intended to limit the scope of this patent. Rather, the inventors have contemplated that the claimed subject matter also might be embodied in other ways, to include different elements or combinations of elements similar to the ones described in this document, in conjunction with other present or future technologies.

In the following description, numerous specific details are set forth, such as examples of specific components, devices, methods, and the like, in order to provide a thorough understanding of embodiments of the present disclosure. It will be understood and appreciated, however, by one skilled in the art that these specific details need not be employed to practice embodiments hereof. In other instances, well-known materials or methods have not been described in detail in order to avoid unnecessarily obscuring embodiments of the present disclosure. While embodiments of the present disclosure are susceptible to various modifications and alternative forms, specific embodiments thereof are shown by way of example in the drawings and herein will be described in detail. It should be understood, however, that there is no intent to limit aspects hereof to the particular forms disclosed, but on the contrary, the intention is to cover all modifications, equivalents, and alternatives falling within the spirit and scope of the disclosure.

It is to be understood that the present disclosure may be implemented in various forms of hardware, software, firmware, special purpose processors, or a combination thereof. Preferably, embodiments of the present disclosure are implemented in software as a program tangibly embodied on a program storage device. The program may be uploaded to, and executed by, a machine comprising any suitable architecture. Preferably, the machine is implemented on a computer platform having hardware such as one or more central processing units (CPUs), a random access memory (RAM), and input/output (I/O) interface(s). The computer platform also includes an operating system and microinstruction code. The various processes and functions described herein either may be part of the microinstruction code or part of the program (or a combination thereof) which is executed via the operating system. In addition, various other peripheral devices may be connected to the computer platform such as an additional data storage device and a printing device. If written in a programming language conforming to a recognized standard, sequences of instructions designed to implement the methods can be compiled for execution on a variety of hardware platforms and for interface to a variety of operating systems. In addition, embodiments of the present framework are not described with reference to any particular programming language. It will be appreciated that a variety of programming languages may be used to implement embodiments of the present disclosure.

It is to be further understood that since at least a portion of the constituent system modules and method steps depicted in the accompanying figures may be implemented in software, the actual connections between the system components (or the flow of the process steps) may differ depending on the manner in which embodiments of the present disclosure are programmed. Given the teachings herein, one of ordinary skill in the related art will be able to contemplate these and similar implementations or configurations of embodiments of the present disclosure The present disclosure relates to a framework for providing a Unified Medical Record (UMR) Cloud Network that takes maintenance and access of patient-centric clinical/healthcare records to the next level by providing a healthcare-app-host-specific app store in a healthcare web portal by utilizing Fast Healthcare Interoperability Resources (FHIR) resources. (FHIR is a standard describing data formats and elements (known as "resources") and an Application Programming Interface (API) for exchanging electronic clinical/healthcare records. FHIR is agnostic to the format of electronic clinical records and, accordingly, serves to integrate records that may be maintained by providers utilizing different data management systems. FHIR is known to those having ordinary skill in the art and, accordingly, is not further described herein.) In aspects, the UMR Cloud Network serves as a patient web portal which hosts a FHIR app store specific to a healthcare app host. The FHIR apps that reside in the healthcare-app-host-specific FHIR app store may be designed to utilize patient-centric data (i.e., healthcare and/or other clinically-relevant data associated with a subject patient) and the subject patient's associated FHIR resources to provide individual solutions. In embodiments, the FHIR apps installed from the healthcare-app-host-specific FHIR app store may be presented on a dashboard associated with the subject patient and provided by the UMR Cloud Network. Thus, the UMR Cloud Network allows the utilization of FHIR resources of a patient and enables an app-store approach specifically for FHIR. This enables patients to have a web portal containing apps that provide individual, customized solutions. The web portal aims at eliminating the need for a patient to maintain medical documentation, clinical reports, medication history reports, medical consultation history, etc. over his/her lifespan. The FHIR RESTful APIs enable the UMR Cloud Network and the hosted FHIR apps to process and provide customized solutions. The UMR architecture also enables developers (provider and/or third-party) with UMR APIs to develop FHIR apps.

Accordingly, aspects of the present disclosure relate a method for customizing healthcare app offerings for a specific patient. The method includes receiving a request from a patient to access a patient-specific, web-based healthcare portal; accessing at least a portion of a clinical record associated with the patient; responsive to accessing the clinical record associated with the patient, determining at least one app relevant to the patient; and presenting a link to the at least one app in association with the patient-specific, web-based healthcare portal.

Aspects of the present disclosure further relate to a method for presenting customized healthcare app offerings. The method includes receiving a request from a client to permit presentation of indicators representing one or more of a plurality of available apps in a patient-specific healthcare portal when clinical records associated with patients indicate an association with the client; receiving a request from patient to access the patient-specific healthcare portal; accessing at least a portion of a clinical record associated with the patient; determining, responsive to accessing the portion of the clinical record associated with the patient, that the patient is associated with the client; and presenting the indicators representing the one or more of the plurality of available apps in the patient-specific healthcare portal.

Still further, aspects of the present disclosure relate to a system for customizing healthcare app offerings to patients. The system includes a Unified Medical Record (UMR) Cloud Network, a healthcare app host, and an app store. The UMR Cloud Network is configured to permit a patient to access apps that are both selected for patients having at least one particular characteristic documented in a clinical record associated with the patient and that are relevant to the patient. The healthcare app host is configured to select a plurality of apps to offer to clients of the healthcare app host, each of the plurality of apps being healthcare-related. The app store is configured to include the plurality of healthcare-related apps selected by the healthcare app host.

With reference now to FIG. 1, shown is a schematic diagram 100 illustrating a healthcare-app-host-specific app store enabling UMR Cloud Network hosting of healthcare-related FHIR apps, in accordance with aspects hereof. Beginning at the bottom of the diagram 100, a plurality of patients 110 (illustrated as Patient 1," "Patient 2," "Patient 3," and "Patient 4," though it will be understood by those having ordinary skill in the relevant art that any number of patients may utilize the exemplary architecture within the scope of aspects hereof) desires access to their patient-specific web-based healthcare portal driven by an FHIR App Store 112 and FHIR resources. Access to the FHIR App Store 112, which is specific to the Healthcare App Host 116, is provided through the UMR Cloud Network 114.

FIG. 1 illustrates that clients 118a, 118b, 118c of the healthcare app host 116 (e.g., "Hospital 1," "Hospital 2," and "Hospital 3," respectively, as illustrated) select individual solutions (that is, select different apps) from a plurality of apps that are hosted in the healthcare-host-specific app store 112 for surfacing when relevant to a particular patient. In other words, the apps available from the FHIR App Store 112 for surfacing in association with patients of a particular healthcare-app-host client (in this case, "Hospital 1" 118a, "Hospital 2" 118b, and "Hospital 3" 118c) are specified and selected by the respective client 118a, 118b, 118c. In the illustrated example in FIG. 1, the client 118a "Hospital 1" may select to have "App 1," "App 2," and "App 3" from the app store available to its patients when relevant and client 118b "Hospital 2" may select to have "App a," "App b," and "App c" from the app store available to its patients when relevant. Thus, if the clinical records of patient 1 110 contain an indication that he or she has been a patient of Hospital 2 118b but contain no indication that he or she has ever been a patient of Hospital 1 118a, App 1 would not surface in association with Patient 1's dashboard event if App 1 were arguably relevant to Patient 1. This is because App 1 has not been selected by Hospital 2 118b to be surfaced in association with its patients when relevant and Patient 1 110 has not been a patient of Hospital 1 118a which has selected for App 1 to be surfaced when relevant.

Though the apps contained within the healthcare-app-host-specific FHIR App Store 112 remain consistent, the apps that will be surfaced to a given patient 110 (e.g., "Patient 1," "Patient 2," "Patient 3," or "Patient 4") will differ based upon data provided by the given patient's clinical record. For instance, if Patient 1 has previously visited Hospital 1 and Hospital 2, and such is evidenced in his/her clinical record, Patient 1 will have App 1, App 2, App 3, App a, App b, and App c surfaced via his/her patient dashboard, if relevant. However, if Patient 3 has previously visited only Hospital 2 and not Hospital 1 (as evidenced by his/her clinical record), he/she will have only App a, App b, and App c surfaced via his/her patient dashboard. In this way, the apps that are surfaced through the patient-specific web-based healthcare portal flex such that they are customized for each particular patient.

To access the patient's dashboard through the patient-specific web-based healthcare portal hosting the FHIR App Store 112, the patient would log into the UMR Cloud Network 114, the UMR Cloud Network 114 would communicate with the FHIR App Store 112 and the apps available to the patient would surface for the patient. That is, a plurality of patients' data (shown near the bottom of the diagram as "Patient 1," "Patient 2," "Patient 3," and "Patient 4") maintained in electronic clinical records interfaces with the UMR Cloud Network 114. As more fully described below with respect to FIGS. 3 through 14, when a particular patient logs into the UMR Cloud Network 114, the UMR Cloud Network 114 communicates with the healthcare-app-host-specific FHIR App Store 112 (which is visible inside the UMR Cloud Network 114) and the apps that will be visible to the patient are accessed through the FHIR App Store 112.

The Healthcare App Host 116 maintains a plurality of healthcare-related apps in the FHIR App Store 112. Individual clients, e.g., hospitals (or any other clinical setting, provider, etc.), may inform the Healthcare App Host 116 maintaining the FHIR App Store 112 which apps they would like to have surfaced for their patients, when those apps are relevant to a particular patient's healthcare history, conditions, and/or other information contained within the patient's clinical record. In other words, only those apps that are relevant to a particular patient will be presented to that patient upon the patient accessing their information through the UMR Cloud Network 114. In embodiments, clients of the Healthcare App Host 116 (e.g., clinical locations such as hospitals and the like) may utilize apps developed by the Healthcare App Host 116. In embodiments, host clients may utilize apps developed by third-party app developers that are maintained in association with the FHIR App Store 112 maintained by the Healthcare App Host 116. Any and all such variations, and any combination thereof, are contemplated to be within the scope of embodiments of the present disclosure. The apps selected by a host client then are hosted in the FHIR App Store 112 maintained by the Healthcare App Host 116 and accessible through the UMR Cloud Network 114.

It will be understood and appreciated by those having ordinary skill in the art that various host clients, such as, by way of example only, service providers, insurance companies, clinical care providers, and the like, in addition to or instead of clinical facilities, may select the apps for surfacing via a patient's web portal. Any and all such variations, and any combination thereof, are contemplated to be within the scope of embodiments of the present disclosure.

Figure 2:
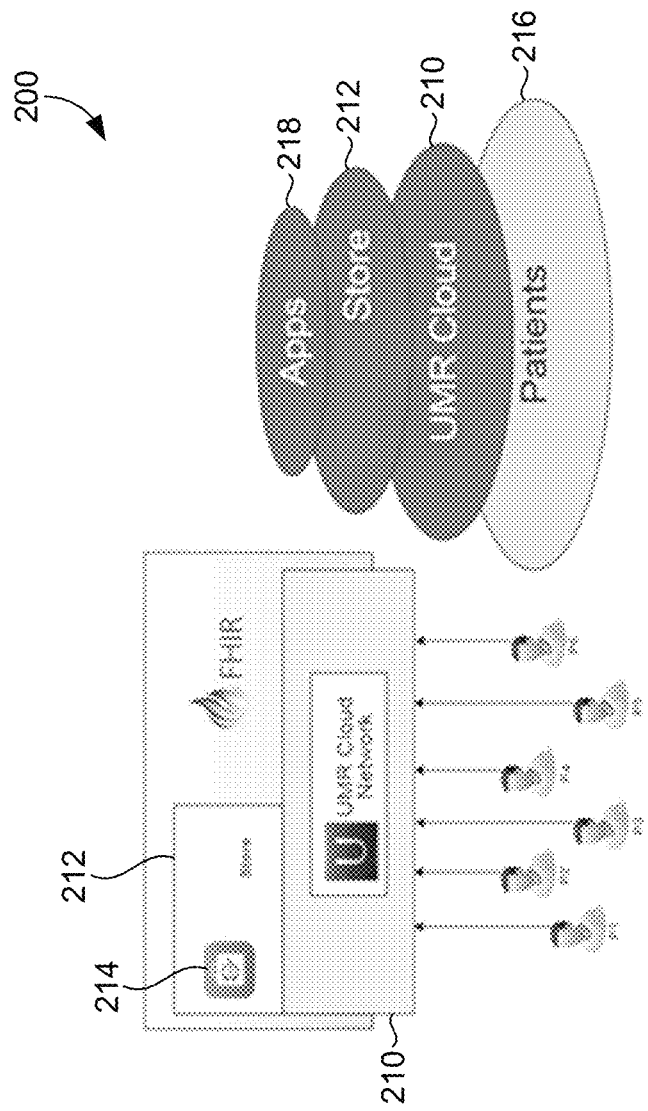
FIG. 2 is a schematic diagram illustrating an exemplary high level system architecture showing UMR cloud network hosting of a healthcare-app-host-specific FHIR App Store, in accordance with embodiments of the present disclosure.

Turning now to FIG. 2, depicted is an exemplary high level system architecture 200 showing UMR Cloud Network 210 hosting of an FHIR App Store 212 maintained by a Healthcare App Host 214 (in this case, Cerner Corporation of North Kansas City, Missouri), in accordance with aspects hereof. As shown, a plurality of patients 216 (also illustrated at P1, P2, P3, P4, P5 and P6, though those skilled in the art will understand that any number of patients may interact with the system architecture 200 in accordance with embodiments of the present disclosure), may log into the UMR Cloud Network 210, the UMR Cloud Network 210 may communicate with the FHIR App Store 212 and the apps 218 available to and relevant for the patient may be presented to the patient, for instance, in association with a dashboard of a patient-specific, web-based healthcare portal. The apps available to the patient may be specified by a provider (e.g., facility, clinician, insurance provider, service provider or the like) associated with the patient as determined from the patient's clinical records. The apps relevant to the patient may be determined based upon information contained within the patient's clinical records such as, for instance, diagnoses, conditions, medications, family history, etc., associated with the patient.

FIGS. 3-14 depict a series of exemplary screen displays representing an exemplary use-case of a UMR Cloud Network, in accordance with embodiments of the present disclosure. In the illustrated example, a patient has been provided appropriate credentials to login to their UMR Cloud Network patient-specific, web-based healthcare portal (for instance, upon visiting a hospital or other clinical setting).

Figure 3:
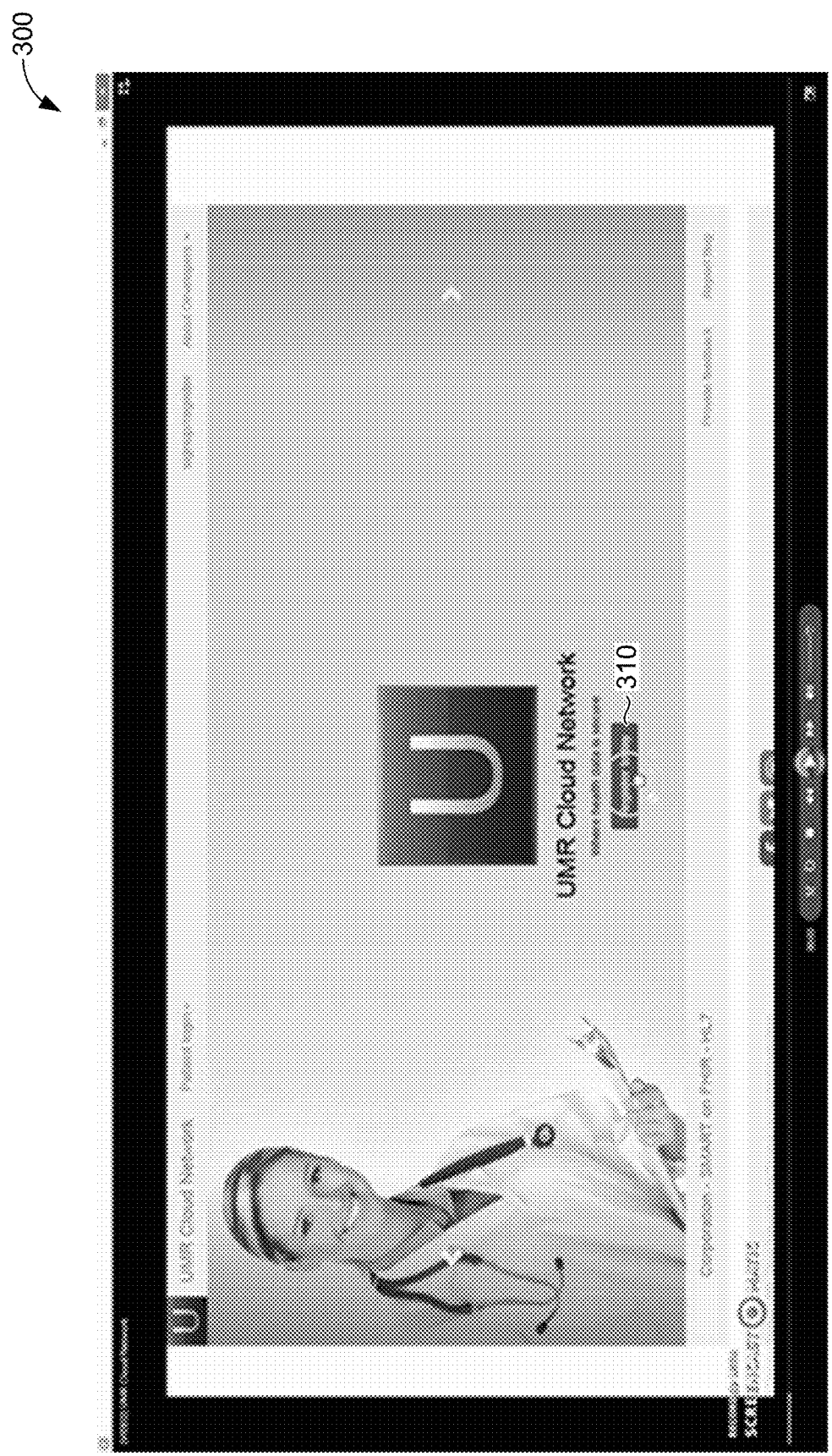
FIG. 3 is an exemplary screen display showing a welcome screen for an exemplary use-case of a healthcare-app-host-specific FHIR App Store enabling UMR Cloud Network hosting of FHIR healthcare-related apps, in accordance with embodiments of the present disclosure.

FIG. 3 depicts an exemplary screen display 300 showing a welcome screen for the exemplary use-case, in accordance with aspects hereof. When a patient/user first logs on to access the UMR Cloud Network, the exemplary welcome screen of FIG. 3 may be provided. As illustrated, a selectable button 310 presenting the words "Register today" is presented. Selection of this button may cause the patient to navigate to the exemplary screen display of FIG. 4.

Figure 4:
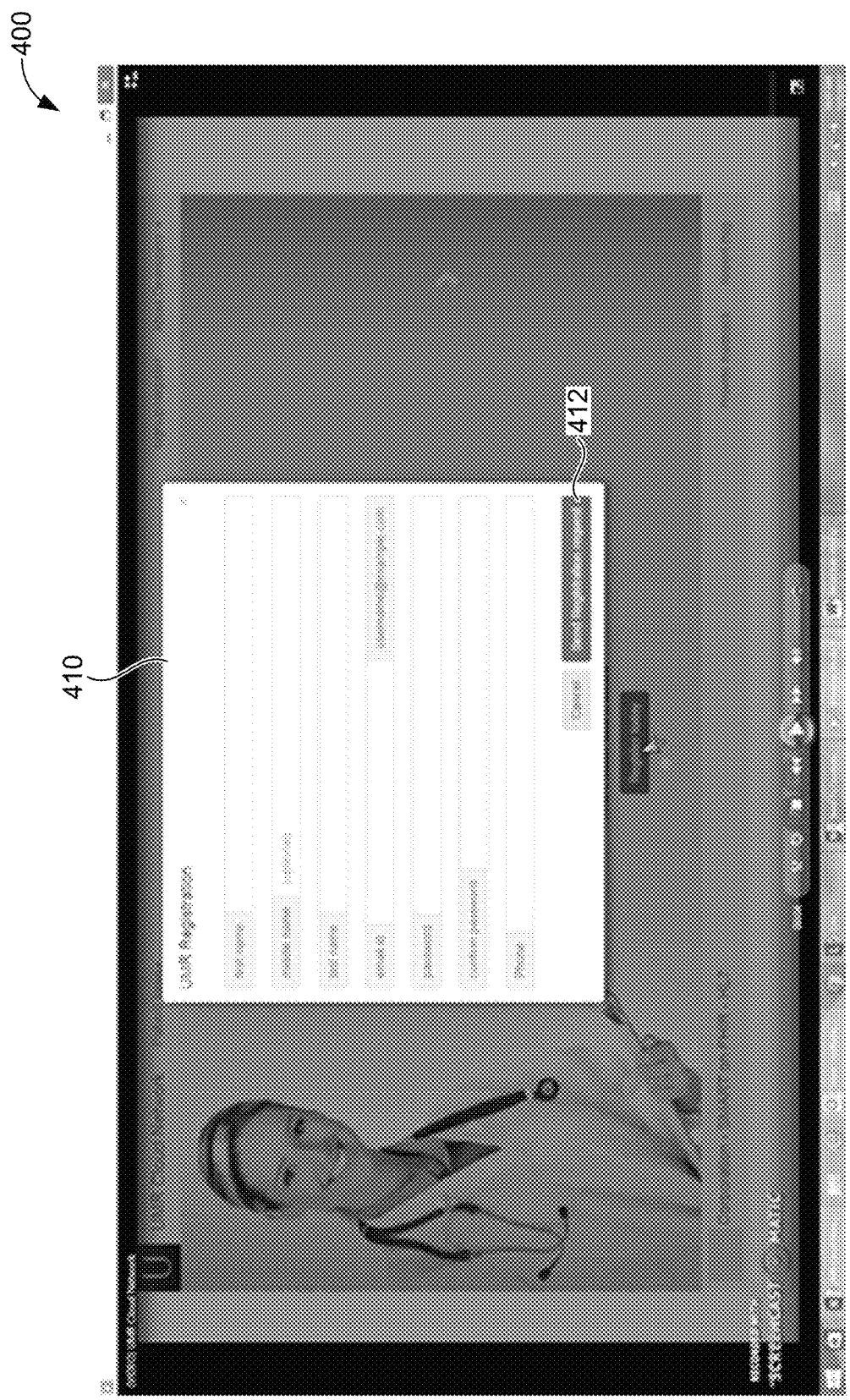
FIG. 4 is an exemplary screen display showing a registration page for an exemplary use-case of a healthcare-app-host-specific FHIR App Store enabling UMR Cloud Network hosting of FHIR healthcare-related apps, in accordance with embodiments of the present disclosure.

FIG. 4 depicts an exemplary screen display 400 showing a registration page 410 for an exemplary use-case, in accordance with aspects hereof. As illustrated, the registration page 410 seeks patient information and instructs the patient to create a password for later access. Upon completion of the required information, the patient may select the button 412 that reads "Send Registration request" to complete the registration process. Once appropriate credentials are created, the user will be able to log in and view his/her customized dashboard, as more fully described below.

Figure 5:
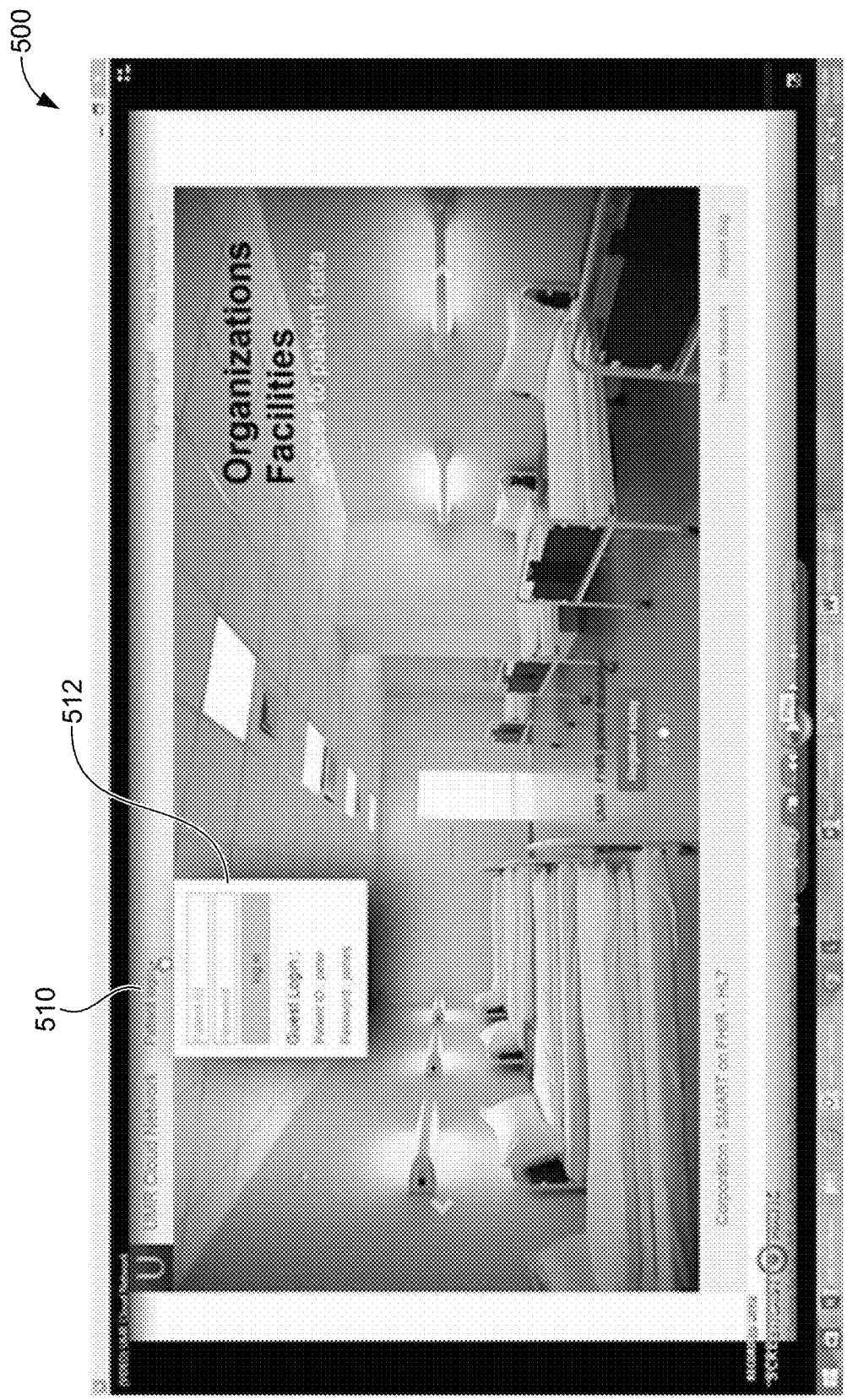
FIG. 5 is an exemplary screen display showing a login screen for an exemplary use-case of a healthcare-app-host-specific FHIR App Store enabling UMR Cloud Network hosting of FHIR healthcare apps, in accordance with embodiments of the present disclosure.

FIG. 5 depicts an exemplary screen display 500 showing a login screen for the exemplary use-case, in accordance with aspects hereof. The illustrative login screen display may be presented to a patient after the patient has created appropriate credentials for logging in (e.g., user name and password). After initial registration, subsequent visits to a clinical setting utilizing the UMR Cloud Network will not require registration but simply login to access patient data. As shown, selection of the button 510 labeled "Patient login" results in presentation of an area 512 in which patients may enter their login credentials.

Figure 6:
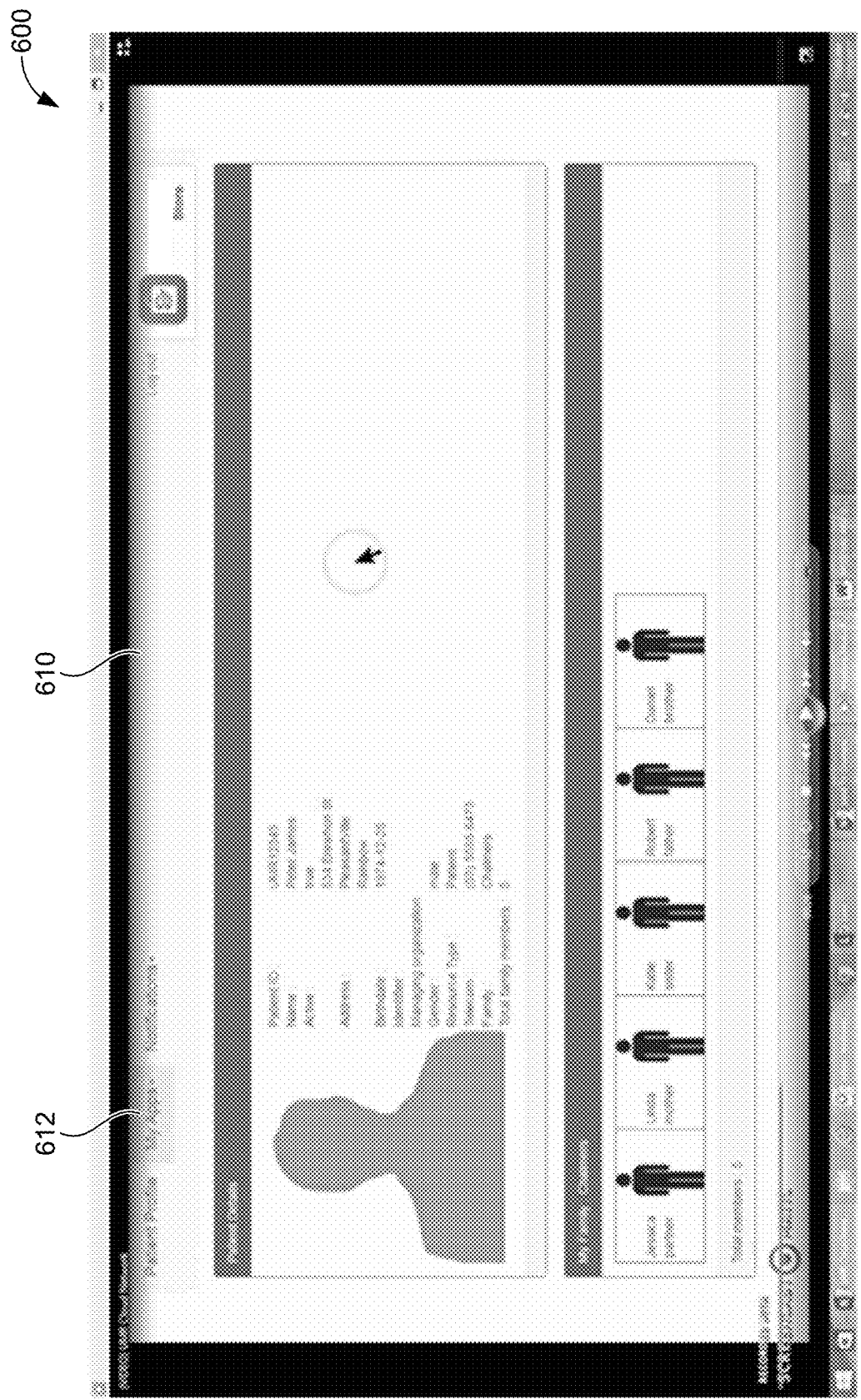
FIG. 6 is an exemplary screen display showing a patient-specific dashboard for an exemplary use-case of a healthcare-app-host-specific FHIR App Store enabling UMR Cloud Network hosting of FHIR healthcare-related apps for a patient by the name of Peter James, in accordance with embodiments of the present disclosure.

FIG. 6 depicts an exemplary screen display 600 showing a patient-specific dashboard for a patient by the name of Peter James, in accordance with aspects hereof. Demographic information about the patient is presented. Links to demographic information for each of the patient's family members also is presented. The top bar 610 of the screen display illustrates a plurality of selectable tabs providing patient-specific information. The tab 612 entitled "My Apps" is highlighted.

Figure 7:
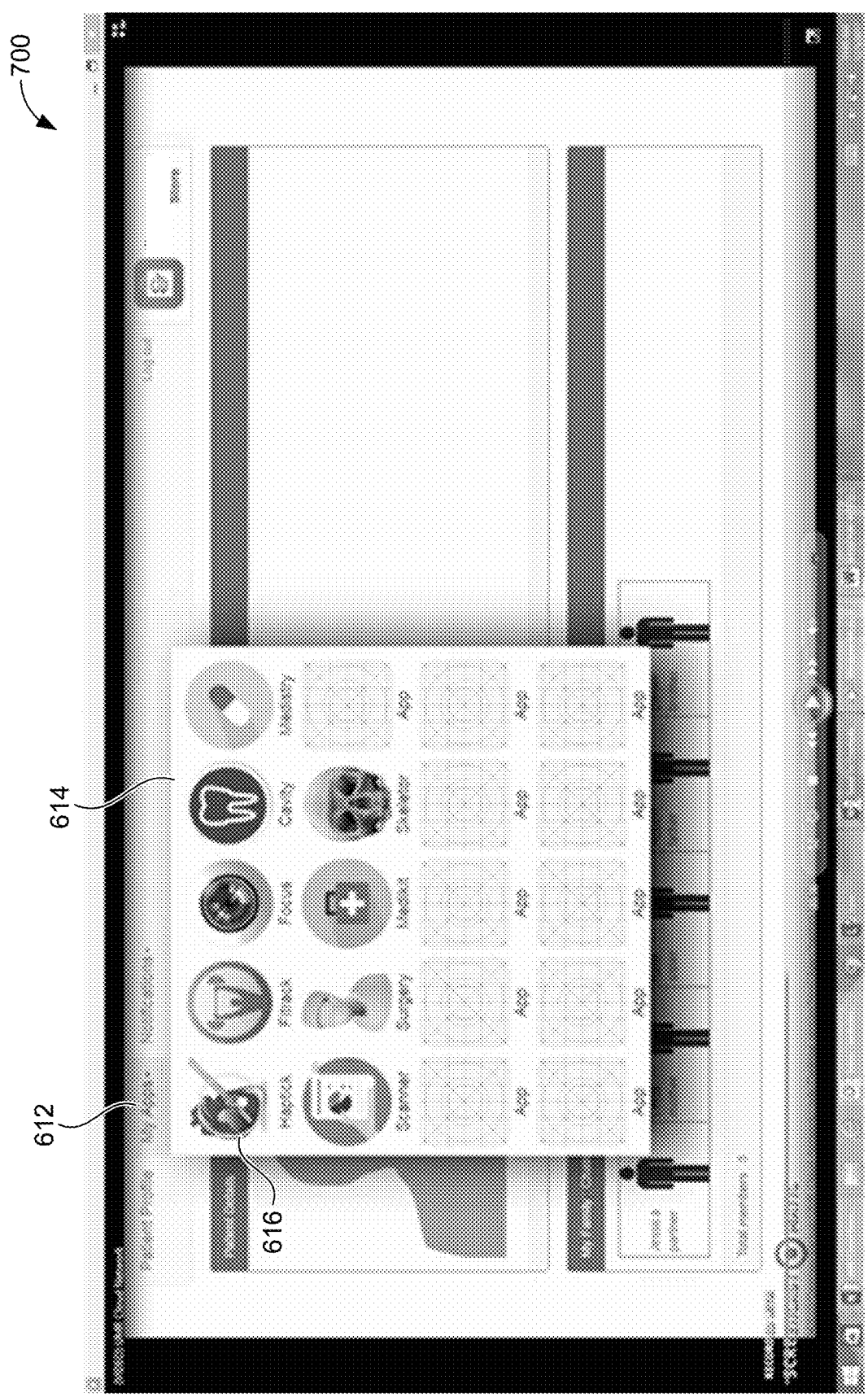
FIG. 7 is an exemplary screen display showing a view presented to the patient, Peter James, upon selection of the "My Apps" tab illustrated in FIG. 6, in accordance with embodiments of the present disclosure.

FIG. 7 depicts an exemplary screen display 700 showing a view presented to the patient, Peter James, upon selection of the "My Apps" tab 612 illustrated in FIG. 6, in accordance with aspects hereof. Illustrated is a viewing area 614 containing apps that have been selected for presentation by one or more providers associated with Peter James, as determined based upon information in his clinical records, and that are relevant for Peter James based upon his diagnoses, medications, history, conditions and the like, also as determined based upon information in his clinical records. That is, the apps presented are presented based upon content in the patient's electronic clinical record and, accordingly, the presented dashboard is customized to the patient, Peter James. As illustrated, the "Haptick" app icon 616 is poised for selection.

Figure 8:
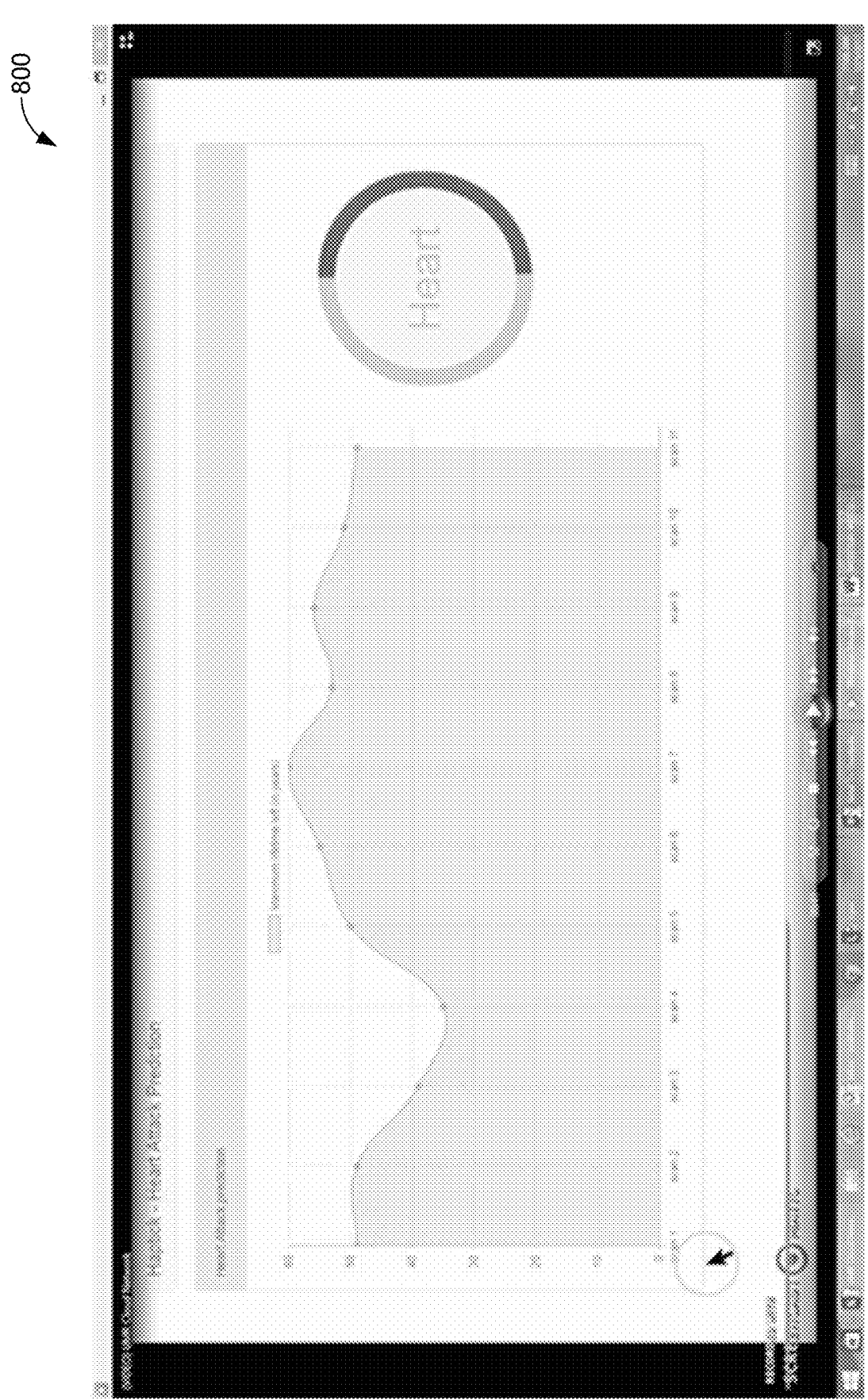
FIG. 8 is an exemplary screen display showing the content that may be viewed by the subject patient upon selection of the "Haptick" app icon of FIG. 7, in accordance with embodiments of the present disclosure.

FIG. 8 depicts an exemplary screen display 800 showing the content that may be viewed by the subject patient upon selection of the "Haptick" app icon 616 of FIG. 7, in accordance with aspects hereof. The information illustrated is based upon data specific to the subject patient and provides a visualization of his predicted heart attack potential. Note that this is not standard data but data that flexes based upon the particular patient's electronic clinical record and, thus, is patient-specific.

Figure 9:
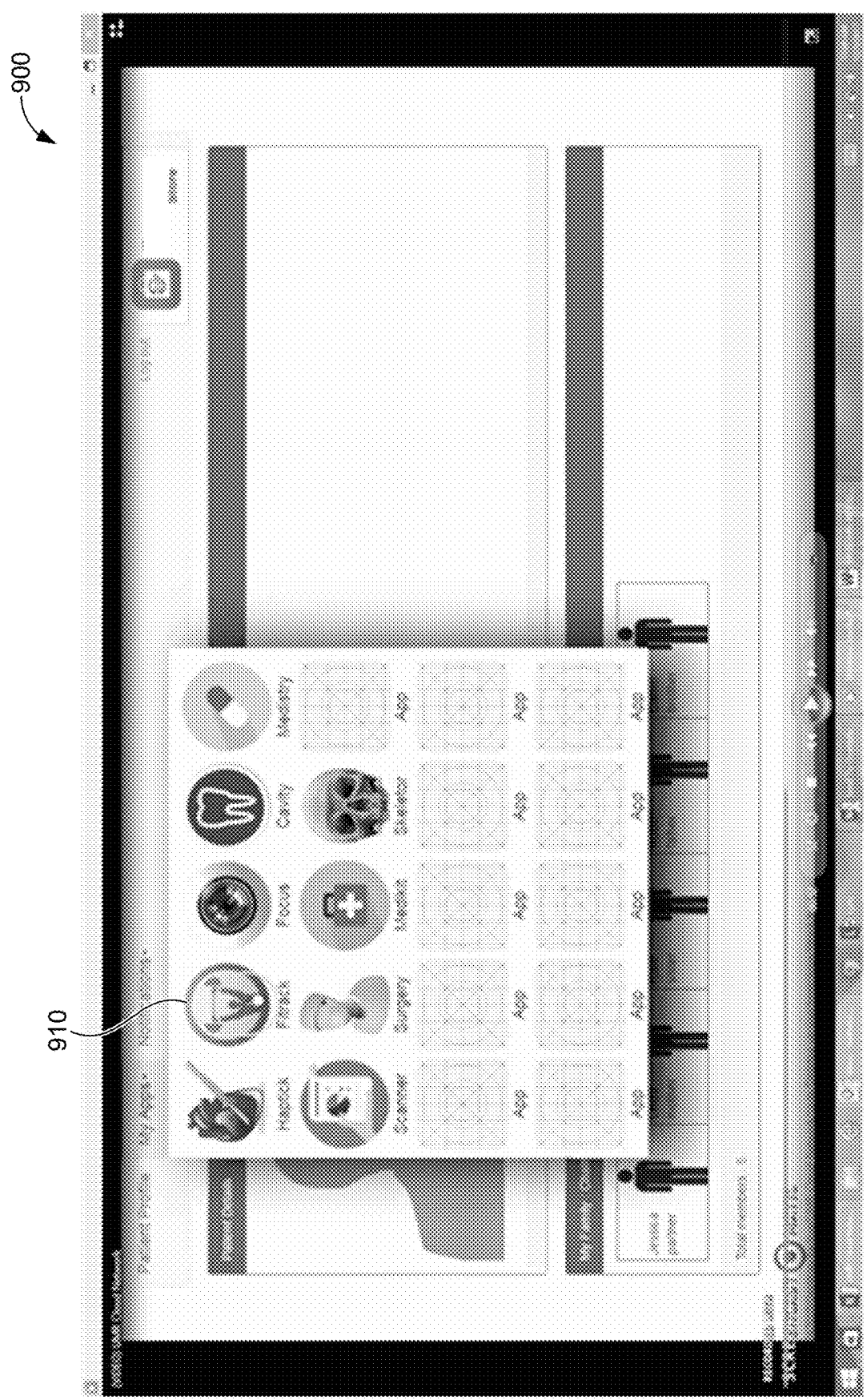
FIG. 9 is an exemplary screen display again showing the apps relevant to and provided for the patient Peter James, in accordance with embodiments of the present disclosure.

FIG. 9 depicts an exemplary screen display 900 again showing a view presented to the patient, Peter James, upon selection of the "My Apps" tab 612 illustrated in FIG. 6, in accordance with aspects hereof. As illustrated, the "Fitrack" app icon 910 is now poised for selection.

Figure 10:
FIG. 10 is an exemplary screen display that may be presented to the patient Peter James upon selection of the "Fitrack" app icon from the patient dashboard of FIG. 9, in accordance with embodiments of the present disclosure.

FIG. 10 depicts an exemplary screen display 1000 that may be presented to the patient Peter James upon selection of the "Fitrack" app icon 910 from the patient dashboard of FIG. 9, in accordance with aspects hereof. Illustrated are a number of muscle areas Peter James has been instructed to exercise, along with his progress in carrying out such fitness exercises. The darker portion of the circumference lines of the circular muscle indicators is indicative of such progress; the larger the dark area, the more progress has been made. Note again that this is not standard data but data that flexes based upon the particular patient's electronic clinical record and, thus, is patient-specific.

Figure 11:
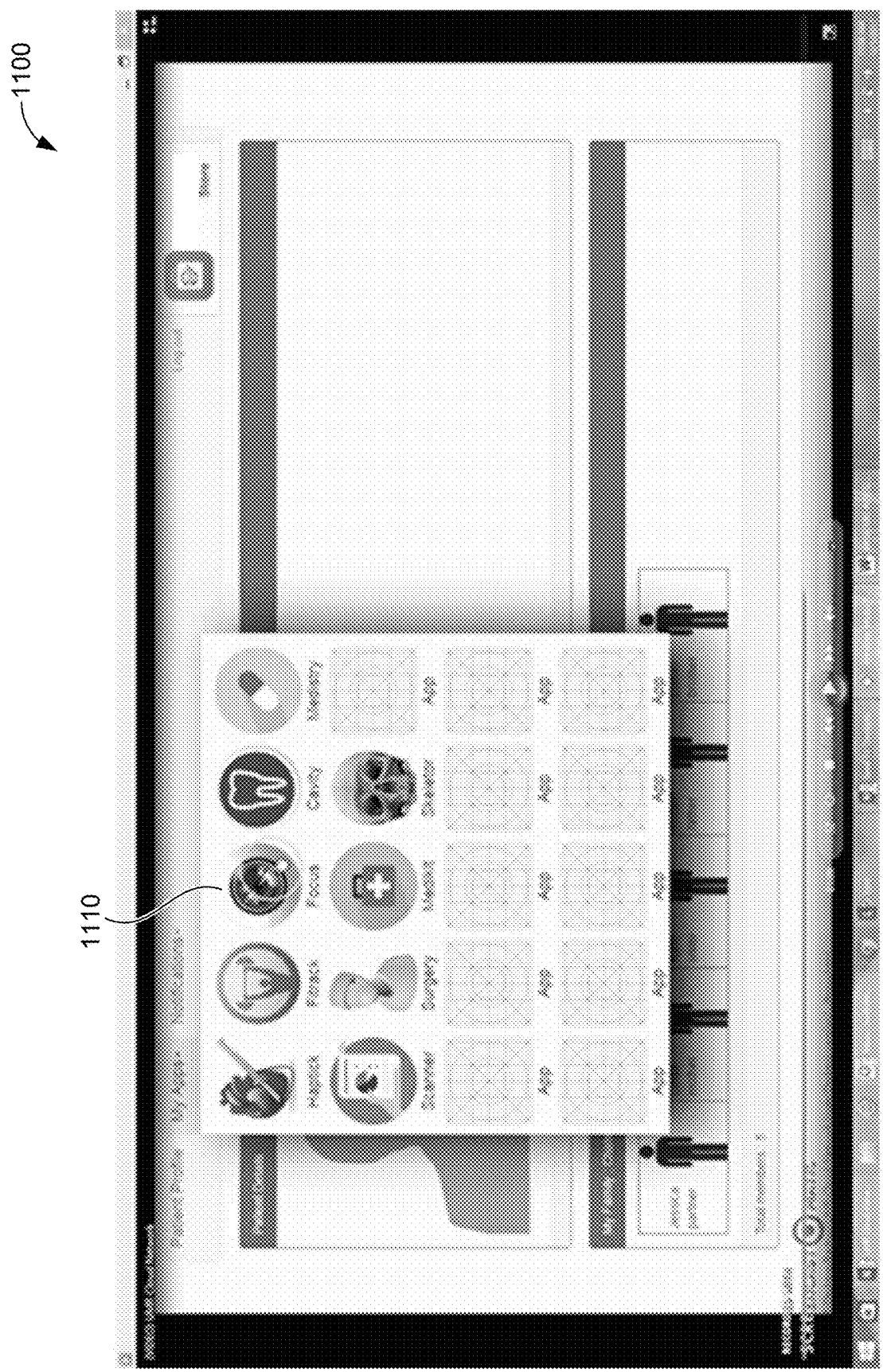
FIG. 11 is an exemplary screen display again showing the apps relevant to and provided for the patient Peter James, in accordance with embodiments of the present disclosure.

FIG. 11 depicts an exemplary screen display 1100 again showing the apps relevant to and provided for the patient Peter James, in accordance with aspects hereof. As illustrated, the "Focus" app icon 1110 is now poised for selection.

Figure 12:
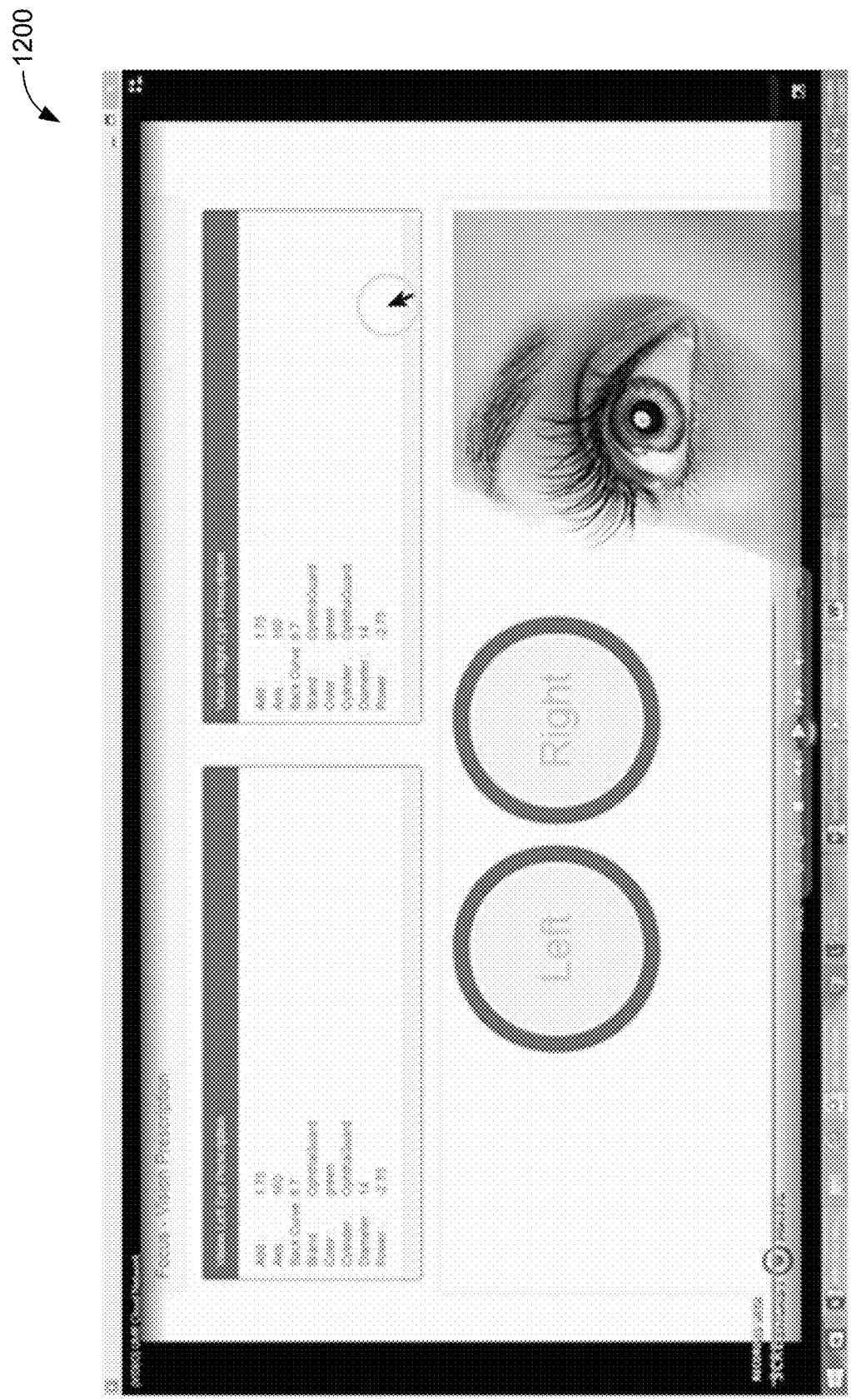
FIG. 12 is an exemplary screen display that may be presented to the patient Peter James upon selection of the "Focus" app icon from the patient dashboard of FIG. 11, in accordance with embodiments of the present disclosure.

FIG. 12 depicts an exemplary screen display 1200 that may be presented to the patient Peter James upon selection of the "Focus" app icon 1110 from the patient dashboard of FIG. 11, in accordance with aspects hereof. Illustrated are Mr. James' most recent vision results from his underlying electronic clinical record. As with prior views (e.g., FIGS. 8 and 10), the data shown is not standard data but data that flexes based upon the particular patient's electronic clinical record and, thus, is patient-specific.

Figure 13:
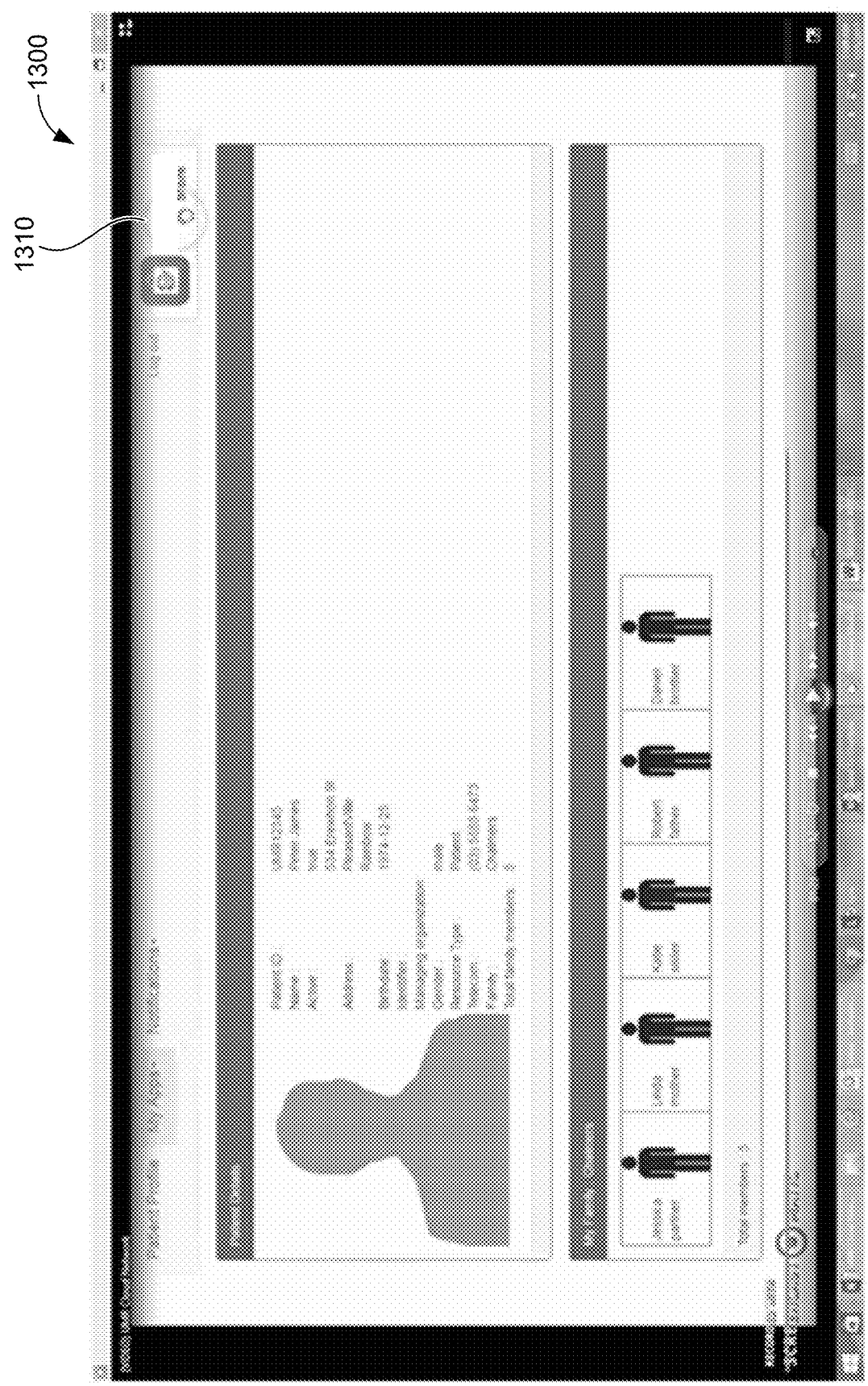
FIG. 13 is an exemplary screen display showing the patient dashboard for the patient Peter James; in accordance with embodiments of the present disclosure.

FIG. 13 depicts an exemplary screen display 1300 showing the patient dashboard for the patient Peter James, in accordance with aspects hereof, the view being similar to that shown in FIG. 6. As illustrated, the "Store" icon 1310 is poised for selection.

Figure 14:
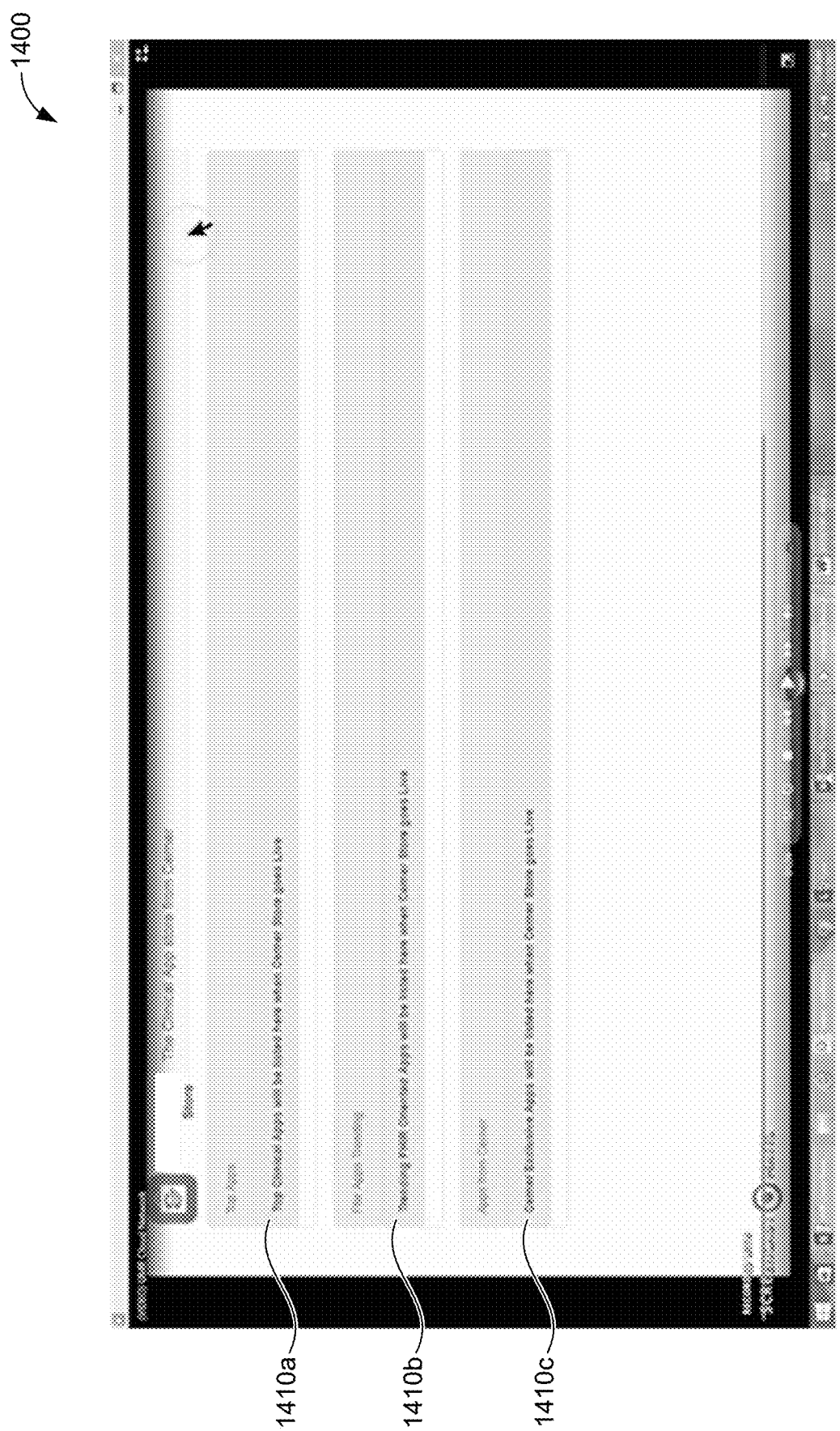
FIG. 14 is an exemplary screen display showing exemplary app categories that may be presented upon selection of the "Store" icon of FIG. 13, in accordance with embodiments of the present disclosure.

FIG. 14 depicts an exemplary screen display 1400 showing exemplary app categories 1410a, 1410b, 1410c that may be presented upon selection of the "Store" icon 1310 of FIG. 13, in accordance with aspects hereof. Notable is that, while no apps are currently presented, the exemplary screen display with app icons will be displayed with the "Top Apps," trending apps and healthcare-app-host developed apps, when such content is available in the healthcare-app-host-specific FHIR App Store (e.g., 112 of FIG. 1).

Figure 15:
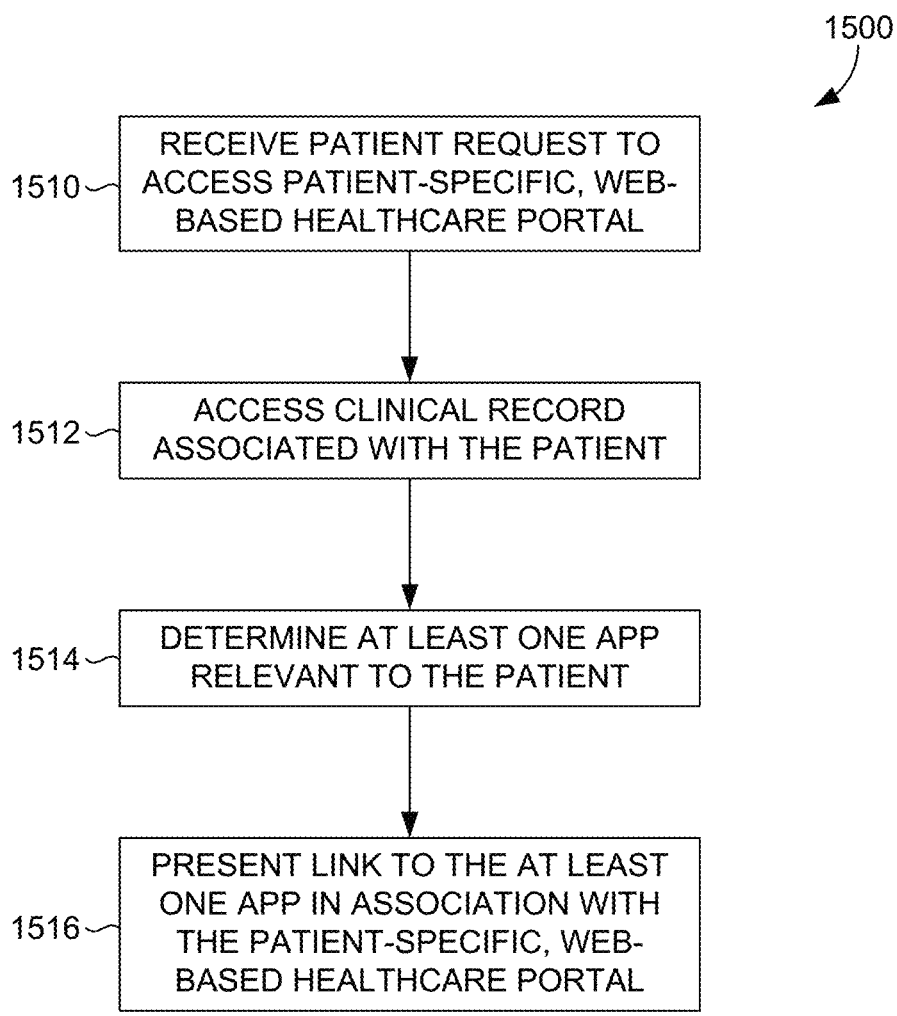
FIG. 15 is a flow diagram illustrating a method for customizing healthcare app offerings, in accordance with embodiments of the present disclosure.

Turning now to FIG. 15, shown is a flow diagram illustrating a method 1500 for customizing healthcare app offerings, in accordance with embodiments of the present disclosure. As indicated at block 1510, a request is received, from a patient, to access a patient-specific, web-based healthcare portal. As indicated at block 1512, at least a portion of a clinical record associated with the patient is accessed. As indicated at block 1514, responsive to accessing the clinical record associated with the patient, at least one app is determined to be relevant to the patient. As indicated at block 1516, a link is presented to the at least one app in association with the patient-specific, web-based healthcare portal.

Figure 16:
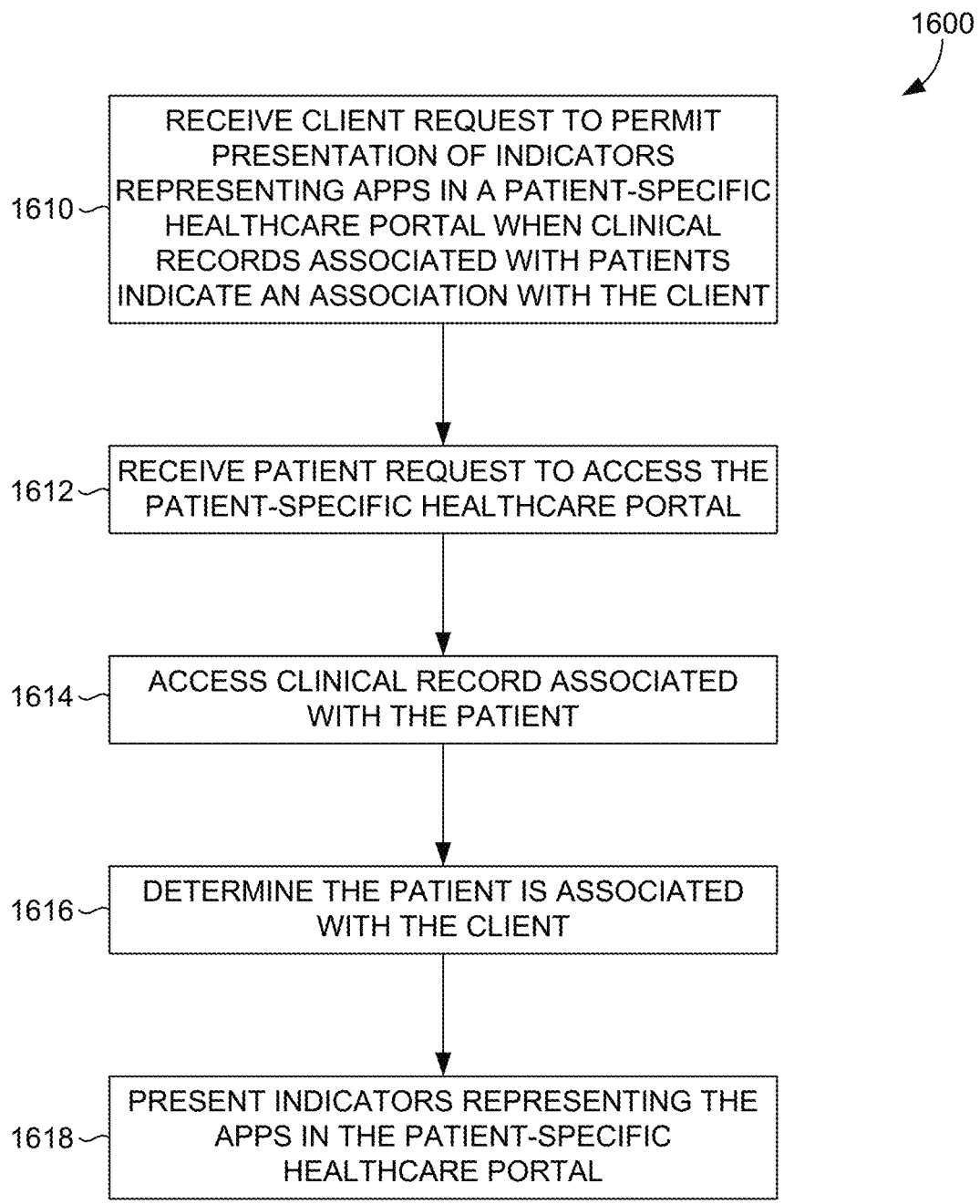
FIG. 16 is a flow diagram illustrating a method for presenting customized healthcare app offerings, in accordance with embodiments of the present disclosure.

With reference to FIG. 16, shown is a flow diagram illustrating a method 1600 for presenting customized healthcare app offerings, in accordance with embodiments of the present disclosure. As indicated at block 1610, a request is received, from a client, to permit presentation of indicators representing one or more of a plurality of available apps in a patient-specific healthcare portal when clinical records associated with patients indicate an association with the client. As indicated at block 1612, a request is received from a patient to access the patient-specific healthcare portal. As indicated at block 1614, at least a portion of a clinical record associated with the patient is accessed. As indicated at block 1616, responsive to accessing the portion of the clinical record associated with the patient, it is determined that the patient is associated with the client. As indicated at block 1618, indicators representing one or more of the plurality of available apps are presented in the patient-specific healthcare portal.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment also can be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings and described herein in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

It is therefore intended that the foregoing detailed description be regarded as illustrative rather than limiting, and that it be understood that it is the following claims, including all equivalents, that are intended to define the spirit and scope of this invention.

What is claimed is:

1. A method comprising:
receiving a request from a device associated with a particular patient to access a web-based portal that hosts a plurality of Fast Healthcare Interoperability Resources (FHIR) computer applications available for a plurality of patients, wherein the plurality of FHIR computer applications are format agnostic, wherein the request communicates unique credentials for the particular patient to a cloud-based Unified Medical Record Network;
responsive to the request, accessing a clinical record that is associated with the particular patient based on the unique credentials;
responsive to accessing the clinical record associated with the particular patient, determining the particular patient is associated with a particular healthcare provider;
determining a set of relevant computer applications from the plurality of FHIR computer applications that are relevant to the particular patient based on the particular healthcare provider defining at least one FHIR computer application to be relevant to at least one of a condition and a medication as documented in the clinical record that is associated with the particular patient, wherein the set of relevant computer applications includes at least one FHIR computer application;
generating a link for each application in the set of relevant computer applications that points to the corresponding computer application within the web-based portal;
providing, via the cloud-based Unified Medical Record Network and based on the unique credentials, access to the web-based portal in a graphical user interface at the device associated with the particular patient;
generating a dashboard, on the graphical user interface, that includes a plurality of selectable tabs that are associated with patient information based on at least the clinical record associated with the particular patient;
wherein the plurality of selectable tabs include an app tab that is configured to contain the links to the set of relevant computer applications relevant to the particular patient; and
in response to receiving an indication of the app tab being selected within the graphical user interface of the web-based portal:
generating and displaying in the graphical user interface of the web-based portal at the device associated with the particular patient, a selectable icon for each of the links to the set of relevant computer applications, wherein upon selection of the selectable icon, a corresponding relevant computer application is executed;
wherein the dashboard and the app tab are customized for the particular patient as providing the selectable icon for the links to the set of relevant computer applications determined to be relevant to the condition and the medication in the clinical record of the particular patient.

2. The method of claim 1, wherein receiving the request comprises receiving the request from the particular patient to access the web-based portal via a cloud network.

3. The method of claim 1, wherein determining the set of relevant computer applications is relevant is based, at least in part, upon one or more computer applications specified by a facility, a clinician, or a healthcare service provider documented in the clinical record that is associated with the particular patient.

4. The method of claim 1, wherein determining that the set of relevant computer applications is relevant is based, at least in part, upon a clinical diagnosis, a medication, a symptom, or a family history stored in the clinical record that is associated with the particular patient.

5. The method of claim 1, wherein the set of relevant computer applications is based upon Fast Healthcare Interoperability Resources.

6. The method of claim 1, wherein the particular healthcare provider is a host of the web-based portal.

7. The method of claim 1, wherein the link is generated within the dashboard.

8. The method of claim 7, wherein the dashboard is accessible via a cloud network.

9. One or more non-transitory computer-readable media having executable instructions embodied thereon that, when executed by a processor of a computing device, cause the computing device to perform actions comprising:
receiving a request from a device associated with a particular patient to access a web-based portal that hosts a plurality of Fast Healthcare Interoperability Resources (FHIR) computer applications available for a plurality of patients, wherein the plurality of FHIR computer applications are format agnostic, wherein the request communicates unique credentials for the particular patient to a cloud-based Unified Medical Record Network;
responsive to the request, accessing a clinical record that is associated with the particular patient based on the unique credentials;
responsive to accessing the clinical record associated with the particular patient, determining the particular patient is associated with a particular healthcare provider;
determining a set of relevant computer applications from the plurality of FHIR computer applications that are relevant to the particular patient based on the particular healthcare provider defining the at least one FHIR computer application to be relevant to at least one of a condition and a medication as documented in the clinical record that is associated with the particular patient, wherein the set of relevant computer applications includes at least one FHIR computer application;
generating a link for each application in the set of relevant computer applications that points to the corresponding computer application within the web-based portal;
providing, via the cloud-based Unified Medical Record Network and based on the unique credentials, access to the web-based portal in a graphical user interface at the device associated with the particular patient;
generating a dashboard, on the graphical user interface, that includes a plurality of selectable tabs that are associated with patient information based on at least the clinical record associated with the particular patient;
wherein the plurality of selectable tabs include an app tab that is configured to contain the links to the set of relevant computer applications relevant to the particular patient; and
in response to receiving an indication of the app tab being selected within the graphical user interface of the web-based portal:
generating and displaying in the graphical user interface of the web-based portal at the device associated with the particular patient, a selectable icon for each of the links to the set of relevant computer applications, wherein upon selection of the selectable icon, a corresponding relevant computer application is executed;

wherein the dashboard and the app tab are customized for the particular patient as providing the selectable icon for the links to the set of relevant computer applications determined to be relevant to the condition and the medication in the clinical record of the particular patient.

10. The media of claim 9, wherein the executable instructions for receiving the request comprises receiving the request from the device associated with the particular patient via the cloud-based Unified Medical Record Network the network.

11. The media of claim 9, wherein receiving the request comprises receiving the request through the web-based portal via the cloud-based Unified Medical Record Network.

12. The media of claim 9, wherein the set of relevant computer applications from the plurality of FHIR computer applications is determined to be relevant to the particular patient prior to providing access to the web-based portal in the graphical user interface at the device associated with the particular patient.

13. The media of claim 9, wherein the set of relevant computer applications from the plurality of FHIR computer applications is determined to be relevant to the particular patient based on at least one characteristic documented in the clinical record that is associated with the particular patient, wherein the at least one characteristic is a clinical diagnosis, a condition, a medication, a symptom, or a family history documented in the clinical record.

14. The media of claim 9, wherein each of the plurality of FHIR computer applications is based upon Fast Healthcare Interoperability Resources.

15. The media of claim 9, further comprising executable instructions for:
restricting presentation of an indicator of one or more of the plurality of FHIR computer applications in the web-based portal.

16. A system comprising:
a healthcare host implemented using one or more processing units configured to select a plurality of Fast Healthcare Interoperability Resources (FHIR) computer applications that are available for a plurality of patients for a plurality of healthcare providers;
a web-based portal that hosts the plurality of Fast Healthcare Interoperability Resources (FHIR) computer applications available for the plurality of patients, wherein the plurality of FHIR computer applications are selected by the healthcare host, wherein the plurality of FHIR computer applications are format agnostic; and
a cloud-based Unified Medical Record Network that provides the plurality of patients access to the web-based portal;
wherein the system is configured to:
receive a request from a device associated with a particular patient to access the web-based portal, wherein the request communicates unique credentials for the particular patient to the cloud-based Unified Medical Record Network;
responsive to the request, access a clinical record that is associated with the particular patient based on the unique credentials;
responsive to accessing the clinical record associated with the patient, determine the particular patient is associated with a particular healthcare provider;
determine a set of relevant computer applications from the plurality of FHIR computer applications that are relevant to the particular patient based on the particular healthcare provider defining the at least one FHIR computer application to be relevant to at least one of a condition and a medication as documented in the clinical record that is associated with the particular patient, wherein the set of relevant computer applications includes at least one FHIR computer application;
generate a link for each application in the set of relevant computer applications that points to the corresponding computer application within the web-based portal;
provide, via the cloud-based Unified Medical Record Network and based on the unique credentials, access to the web-based portal in a graphical user interface at the device associated with the particular patient;
generate a dashboard, on the graphical user interface, that includes a plurality of selectable tabs that are associated with patient information based on at least the clinical record associated with the particular patient;
wherein the plurality of selectable tabs include an app tab that is configured to contain the links to the set of relevant computer applications relevant to the particular patient; and
in response to receiving an indication of app tab being selected within the graphical user interface of the web-based portal:
generating and displaying in the graphical user interface of the web-based portal at the device associated with the particular patient, a selectable icon for each of the links to the set of relevant computer applications, wherein upon selection of the selectable icon, a corresponding relevant computer application is executed;
wherein the dashboard and the app tab are customized for the particular patient as providing the selectable icon for the links to the set of relevant computer applications determined to be relevant to the condition and the medication in the clinical record of the particular patient.

17. The system of claim 16, wherein the system is configured to determine the set of relevant computer applications from the plurality of FHIR computer applications to be relevant to the particular patient based on at least one characteristic documented in the clinical record that is associated with the particular patient, wherein the at least one characteristic is a clinical diagnosis, a condition, a medication, a symptom, or a family history documented in the clinical record.

18. The system of claim 16, wherein each of the plurality of FHIR computer applications is based upon Fast Healthcare Interoperability Resources.

19. The system of claim 16, wherein the system is configured to access the clinical record that is associated with the particular patient and determine whether the particular patient is associated with at least one particular characteristic documented in the clinical record.

20. The system of claim 16, wherein the system is configured to, prior to providing access to the web-based portal in the graphical user interface at the device associated with the particular patient, determine whether the set of relevant computer applications is relevant to the particular patient.

* * * * *